(12) United States Patent
Sasaki et al.

(10) Patent No.: US 10,252,830 B2
(45) Date of Patent: Apr. 9, 2019

(54) ELECTRON BEAM STERILIZATION APPARATUS

(71) Applicant: HITACHI ZOSEN CORPORATION, Osaka (JP)

(72) Inventors: Kazuaki Sasaki, Osaka (JP); Takayasu Yokobayashi, Osaka (JP); Shinichi Takeda, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 0 days.

(21) Appl. No.: 15/518,883

(22) PCT Filed: Oct. 5, 2015

(86) PCT No.: PCT/JP2015/078148
§ 371 (c)(1),
(2) Date: Apr. 13, 2017

(87) PCT Pub. No.: WO2016/059990
PCT Pub. Date: Apr. 21, 2016

(65) Prior Publication Data
US 2017/0225816 A1 Aug. 10, 2017

(30) Foreign Application Priority Data
Oct. 14, 2014 (JP) .................................. 2014-209570

(51) Int. Cl.
*A61L 2/08* (2006.01)
*B65B 55/08* (2006.01)
(Continued)

(52) U.S. Cl.
CPC ................ *B65B 55/08* (2013.01); *A61L 2/08* (2013.01); *A61L 2/087* (2013.01); *B65B 55/04* (2013.01);
(Continued)

(58) Field of Classification Search
CPC .............. A61L 2/08; A61L 2/087; A61L 2/007
(Continued)

(56) References Cited

U.S. PATENT DOCUMENTS

2005/0158218 A1* 7/2005 Dumargue ................ A23L 3/26
422/121
2011/0016829 A1 1/2011 Drenguis et al.
(Continued)

FOREIGN PATENT DOCUMENTS

CN 102686247 A 9/2012
CN 103889463 A 6/2014
(Continued)

OTHER PUBLICATIONS

International Search Report dated Jan. 12, 2016 for Appln. No. PCT/JP2015/078148.
(Continued)

*Primary Examiner* — Jason L McCormack
(74) *Attorney, Agent, or Firm* — Pillsbury Winthrop Shaw Pittman, LLP

(57) ABSTRACT

One object is to provide an electron beam sterilization apparatus including: an inner-surface sterilization chamber (5) including an inner-surface electron beam application device; and a blocking chamber (6) for receiving a preform product (P) from the inner-surface sterilization chamber (5) and blocking X-rays produced by application of the electron beam. The blocking chamber (6) includes an upstream opening (62) and a downstream opening (63) formed therein, the preform product (P) being received through the upstream opening (62) and transferred through the downstream opening (63). The blocking chamber (6) includes: a gripper (74) for gripping the preform product (P); a sterilized rotation table (71) for conveying the gripped preform product (P) in a circular path; and a blocking wall (81) not
(Continued)

in contact with the sterilized rotation table (71) and configured to block the X-rays.

5 Claims, 8 Drawing Sheets

(51) Int. Cl.
*B65B 55/04* (2006.01)
*G21K 5/00* (2006.01)
*G21K 5/04* (2006.01)
*G21K 5/10* (2006.01)
*G21K 5/08* (2006.01)

(52) U.S. Cl.
CPC ............ *G21K 5/00* (2013.01); *G21K 5/04* (2013.01); *G21K 5/08* (2013.01); *G21K 5/10* (2013.01); *A61L 2202/23* (2013.01)

(58) Field of Classification Search
USPC .................. 250/453.11, 455.11, 396 R, 400
See application file for complete search history.

(56) References Cited

U.S. PATENT DOCUMENTS

| 2013/0001434 | A1 | 1/2013 | Lejeune et al. |
| 2014/0112826 | A1 | 4/2014 | Knott et al. |
| 2014/0231673 | A1* | 8/2014 | Yokobayashi ......... B65B 55/08 250/455.11 |

FOREIGN PATENT DOCUMENTS

| JP | 9-243793 | 9/1997 |
| JP | 2000-214300 | 8/2000 |
| JP | WO 2013058204 A1 * | 4/2013 ............ B65B 55/08 |
| JP | 2014-129139 | 7/2014 |
| WO | WO 97/34305 | 9/1997 |
| WO | WO 2013/058204 | 4/2013 |

OTHER PUBLICATIONS

Extended European Search Report EP Application No. 15850814.3 dated Sep. 19, 2017.
First Office Action Chinese Patent Application No. 201580054287.9 dated Aug. 3, 2018 with English translation.

* cited by examiner

ELECTRON BEAM STERILIZATION APPARATUS

CROSS-REFERENCE TO RELATED APPLICATIONS

This is the U.S. National Stage of PCT/JP2015/078148 filed Oct. 5, 2015, which in turn claims priority to Japanese Application No. 2014-209570, filed Oct. 14, 2014, the entire contents of all applications are incorporated herein by reference in their entireties.

TECHNICAL FIELD

The present invention relates to an electron beam sterilization apparatus for sterilizing, e.g., containers for foods and beverages or medical products by applying an electron beam.

BACKGROUND

If a company handling containers for foods and beverages produces food poisoning due to insufficient sterilization of the containers, the company will significantly lose social credibility. Therefore, in advanced countries where safety of foods and beverages is essential, it is necessary to sterilize containers for foods and beverages securely.

Devices currently used for secure sterilization of containers apply an electron beam to the containers. Although such devices permit secure sterilization of the containers, application of an electron beam to the containers may produce X-rays, which are radioactive and harmful to organisms. Therefore, there has been provided a structure for the above devices in which the X-rays are sufficiently blocked such that the X-rays produced are prevented from being leaked harmfully (see Patent Literature 1). As shown in FIG. 6 of Patent Literature 1, the structure disclosed in Patent Literature 1 includes a blocking member for blocking X-rays. The blocking member has a cylindrical shape and is mounted on a rotation table for conveying containers to a circular path. With this arrangement, the X-rays can be blocked sufficiently, as shown in FIG. 11 of Patent Literature 1.

RELEVANT REFERENCES

Patent Literature

Patent Literature 1: International Publication No. WO 2013/058204.

SUMMARY

There have recently been demands for sterilization devices that apply electron beams to more containers in a shorter period of time, in other words, high speed sterilization devices. However, the sterilization devices disclosed in Patent Literature 1, which includes the blocking member mounted on the rotation table and has a large weight, cannot rotate the rotation table at a high speed and is not capable of increasing the speed. In addition, since the blocking member mounted on the rotation table has a large weight, the blocking member (having a cylindrical shape) needs to have a small diameter so as to stabilize the rotation of the rotation table. Therefore, as shown in FIG. 11 of Patent Literature 1, the sterilization device disclosed in Patent Literature 1 needs to have a large number of rotation tables having a blocking member mounted thereon so as to block the X-rays sufficiently, and thus also needs to have a large number of chambers for housing the rotation tables. Accordingly, the sterilization device of Patent Literature 1 has a large size due to a large number of rotation tables and chambers.

One object of the present invention is to provide an electron beam sterilization apparatus that has a small size and operates at a high speed without harmful leakage of X-rays.

To overcome the above problem, a first aspect of the present invention provides an electron beam sterilization apparatus for sterilizing a container by applying an electron beam while conveying the container, the apparatus comprising: a sterilization chamber including an electron beam application device for applying an electron beam to a container; and a blocking chamber for receiving the container from the sterilization chamber and blocking radioactive rays produced by application of the electron beam, wherein the blocking chamber includes an upstream opening and a downstream opening formed therein, the container being received from the sterilization chamber through the upstream opening and transferred to outside of the blocking chamber through the downstream opening, the blocking chamber includes: a retainer for retaining the container; a rotation table for conveying the container retained by the retainer in a circular path; and at least one blocking wall not in contact with the rotation table and configured to block the radioactive rays from the sterilization chamber, and the at least one blocking wall faces the upstream opening or the downstream opening and has a larger area than the upstream opening or the downstream opening facing thereto.

A second aspect of the present invention provides the electron beam sterilization apparatus of the first aspect, wherein the retainer is attached to a periphery of the rotation table and configured to retain the container outside the periphery of the rotation table, and the at least one blocking wall is arranged within a region outward from the periphery of the rotation table to inside of a circular path in which the container is conveyed by the rotation table.

Further, a third aspect of the present invention provides the electron beam sterilization apparatus of the first or second aspect, wherein the at least one blocking wall extends higher than upper ends of the upstream opening and the downstream opening.

In addition, a fourth aspect of the present invention provides the electron beam sterilization apparatus of the first or second aspect, wherein the at least one blocking wall comprises an upstream blocking wall and a downstream blocking wall, the upstream blocking wall facing the upstream opening and having an area larger than the upstream opening, the downstream blocking wall facing the downstream opening and having an area larger than the downstream opening.

A fifth aspect of the present invention provides the electron beam sterilization apparatus of the fourth aspect, wherein a ventilation space is formed between the upstream blocking wall and the downstream blocking wall.

A sixth aspect of the present invention provides the electron beam sterilization apparatus of the fourth aspect, wherein the upstream blocking wall and the downstream blocking wall are positioned to block all straight lines connecting between the upstream opening and the downstream opening.

A seventh aspect of the present invention provides the electron beam sterilization apparatus of the fourth aspect, wherein no straight lines extending through the upstream opening and an end of the upstream blocking wall intersect, in the blocking chamber, any straight lines extending through the downstream opening and an end of the downstream blocking wall.

Advantages

The above electron beam sterilization apparatus has a small size and operates at a high speed without harmful leakage of X-rays.

DESCRIPTION OF EXAMPLE EMBODIMENTS

Figure 1:
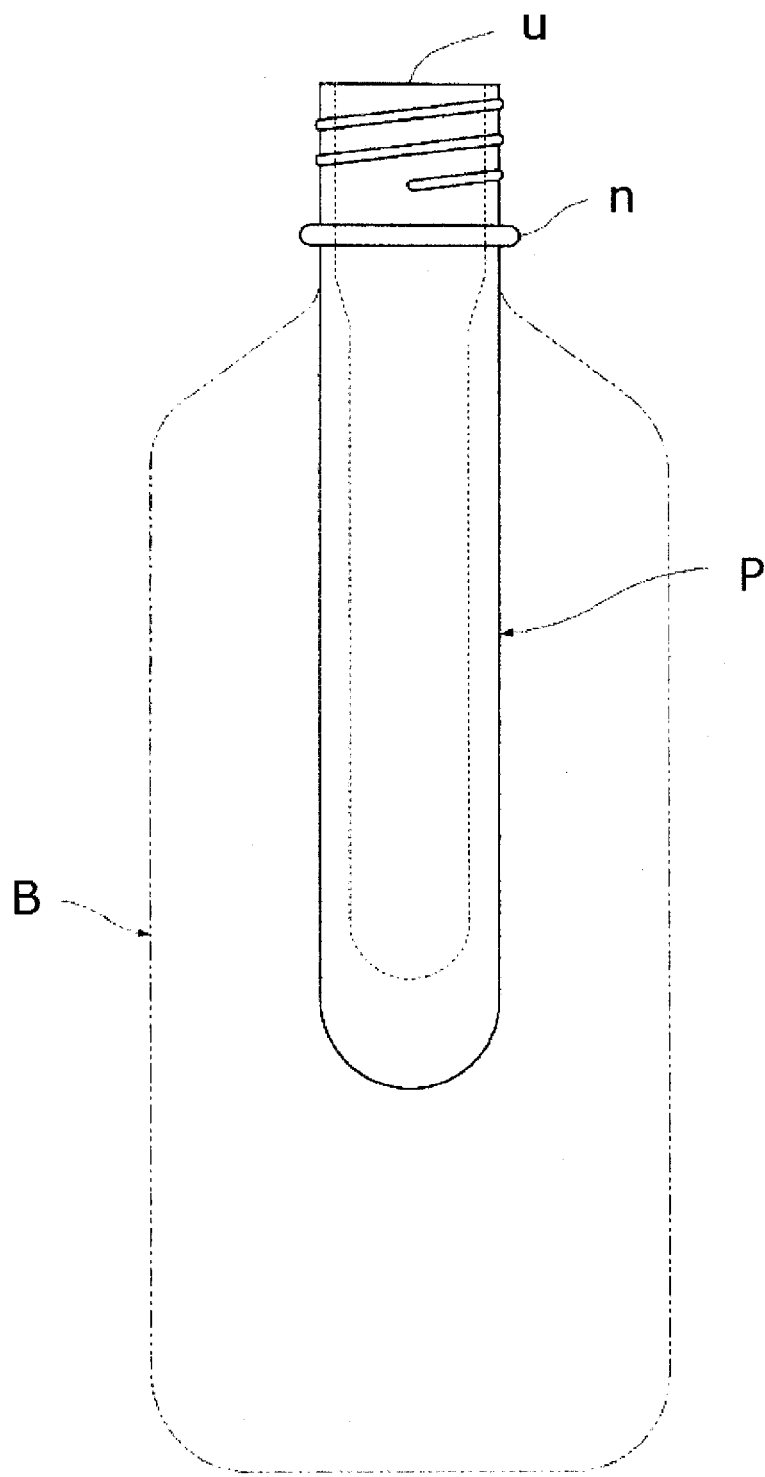
FIG. 1 is a side view of a container to be sterilized with an electron beam sterilization apparatus according to an embodiment of the present invention.

An electron beam sterilization apparatus according to an embodiment of the present invention will be described below with reference to the accompanying drawings. Briefly, the electron beam sterilization apparatus may sterilize containers by applying an electron beam while conveying the containers. In the following description, a preform product P as shown in FIG. 1 is taken as an example of container. The preform product P may be a material prior to being formed into a plastic bottle B by blow molding and may have a test tube shape (having a U shape in a vertical section with an opened top end u).

Figure 2:
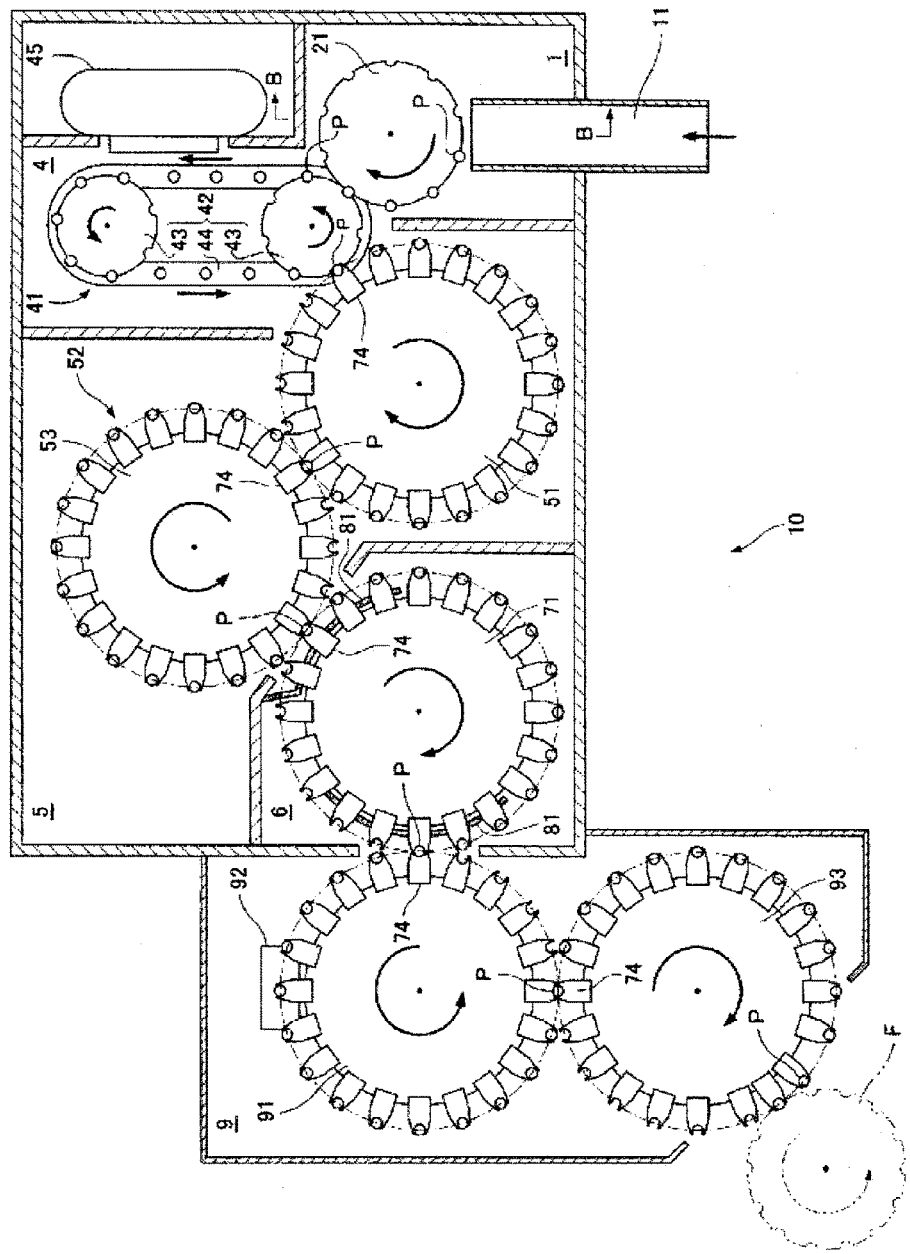
FIG. 2 is a schematic plan view showing an entirety of the electron beam sterilization apparatus.

As shown in FIG. 2, the electron beam sterilization apparatus may schematically include five chambers. These five chambers may include, in the order from the upstream side of the path through which the preform products P are conveyed, a feed chamber 1 into which the preform products P are fed from outside, an outer-surface sterilization chamber 4 in which the outer surfaces of the preform products P are sterilized with electron beams, an inner-surface sterilization chamber 5 in which the inner surfaces of the preform products P are sterilized with electron beams, a blocking chamber 6 for preventing external leakage of X-rays (an example of radioactive rays) produced when the electron beams are applied to the preform products P, and a sorting chamber 9 in which preform products P that are insufficiently sterilized (hereinafter referred to simply as "defective products") are ejected. These five chambers 1, 4, 5, 6, 9 may have a floor, walls, and a ceiling made of a material that blocks X-rays.

The feed chamber 1 may include an input tube 11 for putting in the preform products P and an input star wheel 21 (an example of rotation conveyor plate) from which the preform products P put in through the input tube 11 are conveyed.

The outer-surface sterilization chamber 4 may include an outer-surface sterilization unit 41 for receiving the preform products P from the input star wheel 21 and sterilizing the outer surfaces thereof with electron beams. The outer-surface sterilization unit 41 may include an oval path conveyor 42 and an outer-surface electron beam application device 45. The oval path conveyor 42 may be configured to convey in an oval path the preform products P received from the input star wheel 21, and the outer-surface electron beam application device 45 may be configured to apply an electron beam (having a substantially rectangular cross section) to outer surfaces of the preform products P being conveyed by the oval path conveyor 42. The oval path conveyor 42 may include two outer-surface sterilization star wheels 43 and an endless conveyor belt 44. One of the two outer-surface sterilization star wheels 43 may be positioned near one end of the outer-surface electron beam application device 45 and the other may be positioned near the other end of the same. The endless conveyor belt 44 may be stretched between the two outer-surface sterilization star wheels 43 and configured to convey the preform products P.

The inner-surface sterilization chamber 5 may include a turn rotation table 51 and an inner-surface sterilization unit 52. The turn rotation table 51 may be configured to receive the preform products P from the oval path conveyor 42 and convey them in a circular path, and the inner-surface sterilization unit 52 may be configured to receive the preform products P from the turn rotation table 5 land sterilize the inner surfaces of the preform products P with electron beams. The inner-surface sterilization unit 52 may include an inner-surface sterilization rotation table 53, elevation devices (not shown), and inner-surface electron beam application devices (not shown) provided in the same number as the elevation devices. The inner-surface sterilization rotation table 53 may be configured to convey the preform products P in a circular path. The elevation devices may be provided on the inner-surface sterilization rotation table 53 at a pitch of a central angle (e.g., 18°, or 0.1 πrad) and configured to elevate and lower the preform products P. The inner-surface electron beam application devices may be positioned directly above the elevation devices and configured to apply electron beams (having a substantially circular cross section) to the inner surfaces of the preform products P. Each of the inner-surface electron beam application devices may be provided with a nozzle at its lower end, for emitting an electron beam downward. The inner-surface electron beam application devices may be positioned directly above the associated elevation devices and may be configured to move in the circular path at the same rotation speed as the elevation devices. The elevation devices may be configured to elevate the preform product P so as to insert the nozzle into an opening of the preform product P, and then lower the preform product P so as to pull the nozzle out of the opening of the preform product P. While the nozzle is out of the opening of the preform product P, the preform product P can be received from or transferred to other rotation tables 51, 71.

The blocking chamber 6 may include a sterilized rotation table 71 and blocking walls 81. The sterilized rotation table 71 may be configured to receive preform products P from the inner-surface sterilization rotation table 53 and convey the preform products P in a circular path, and the blocking walls 81 may block the X-rays entering from the inner-surface sterilization chamber 5.

The sorting chamber 9 may include a sorting rotation table 91 and an output rotation table 93. The sorting rotation table 91 may be configured to receive preform products P from the sterilized rotation table 71 and convey the preform products P in a circular path, while sorting the defective products from the others. The output rotation table 93 may be configured to receive the preform products P other than the defective products from the sorting rotation table 91 and convey them in a circular path, finally to output the preform products P. In the floor of the sorting chamber 9 below a part of the circular path of the sorting rotation table 91, there may be provided an outlet 92 through which defective products are ejected. When a preform product P being conveyed in the circular path is determined to be defective, the sorting rotation table 91 may drop the defective product from above the outlet 92. The output rotation table 93 may feed the preform products P other than the defective products to an external apparatus F (e.g., an apparatus for blow molding).

The above-described rotation tables, that is, the turn rotation table 51, the inner-surface sterilization rotation table 53, the sterilized rotation table 71, the sorting rotation table 91, and the output rotation table 93, may be provided with grippers 74 (an example of retainers) for gripping the preform products P at a pitch of a central angle (e.g., 18°, or 0.1 πrad). At a position to receive a preform product P from the upstream side for conveying it in a circular path, the grippers 74 may grip a neck n (see FIG. 1) of the preform product P, and at the position to transfer the preform product P to the downstream side, the grippers 74 may release the preform product P. Thus, the preform product P can be transferred smoothly from the upstream side to the downstream side. The elevation devices provided for the inner-surface sterilization table 53 can elevate or lower the preform products P independently for the associated grippers 74.

In the outer-surface sterilization chamber 4 and the inner-surface sterilization chamber 5, the electron beams may cause a chemical reaction of the air that produces ozone. Ozone may accumulate in the electron beam sterilization apparatus 10 to cause corrosion of the electron beam sterilization apparatus 10. Therefore, the electron beam sterilization apparatus 10 may include a ventilator (not shown) for discharging ozone by pressure difference.

The blocking chamber 6 which constitutes the purport of the present invention will be described in detail with reference to FIGS. 3 to 5.

Figure 3:
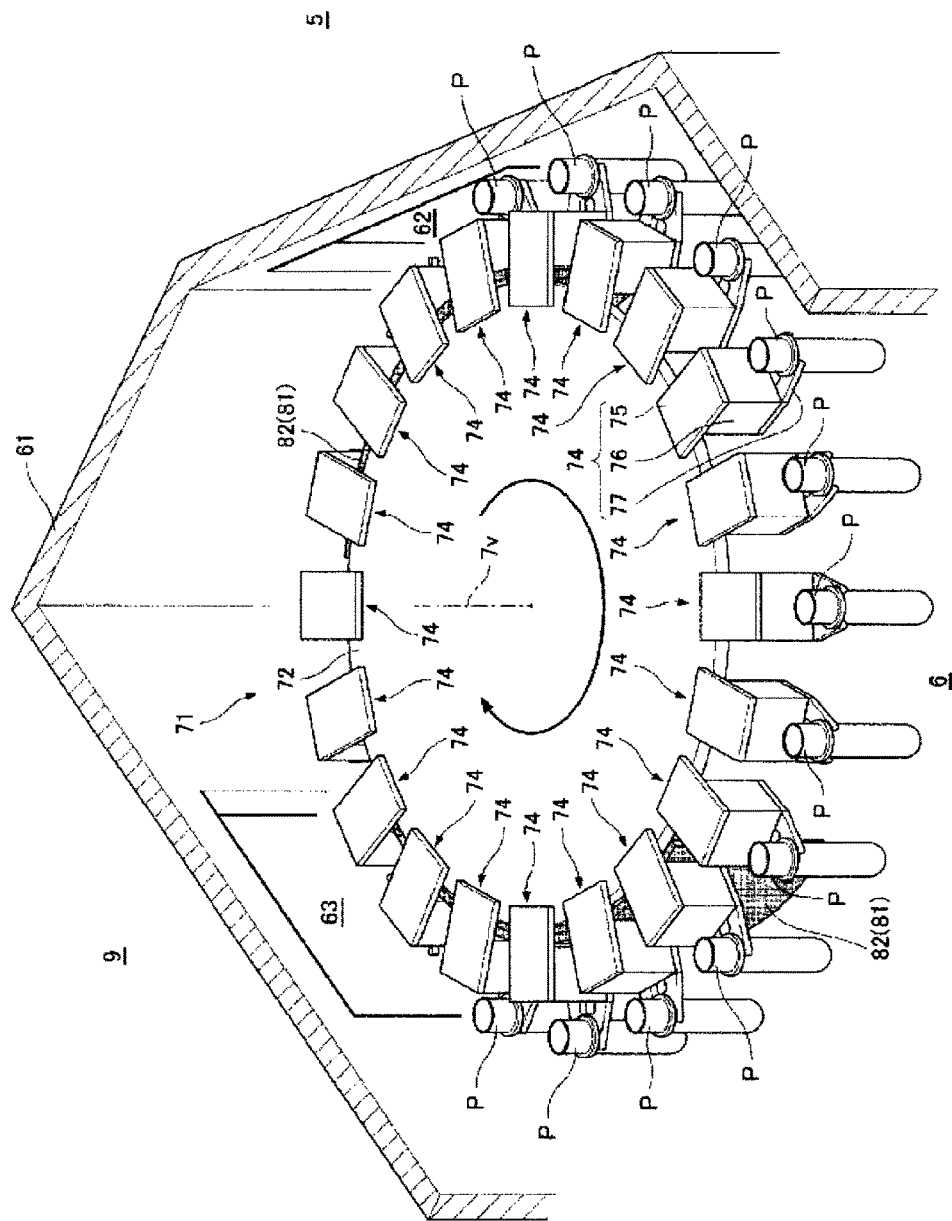
FIG. 3 is a perspective view showing a blocking chamber in the electron beam sterilization apparatus.
Figure 4:
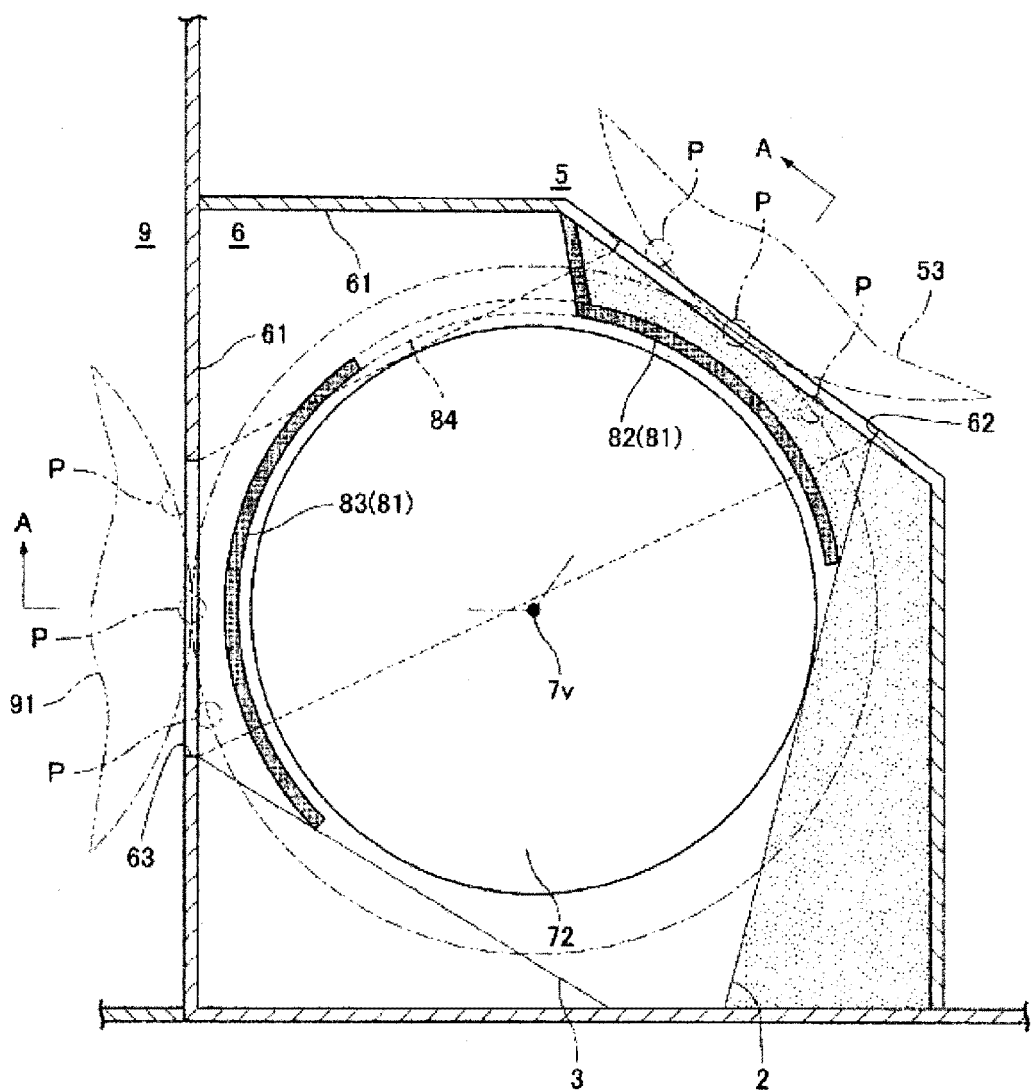
FIG. 4 is a plan view of the blocking chamber.
Figure 5:
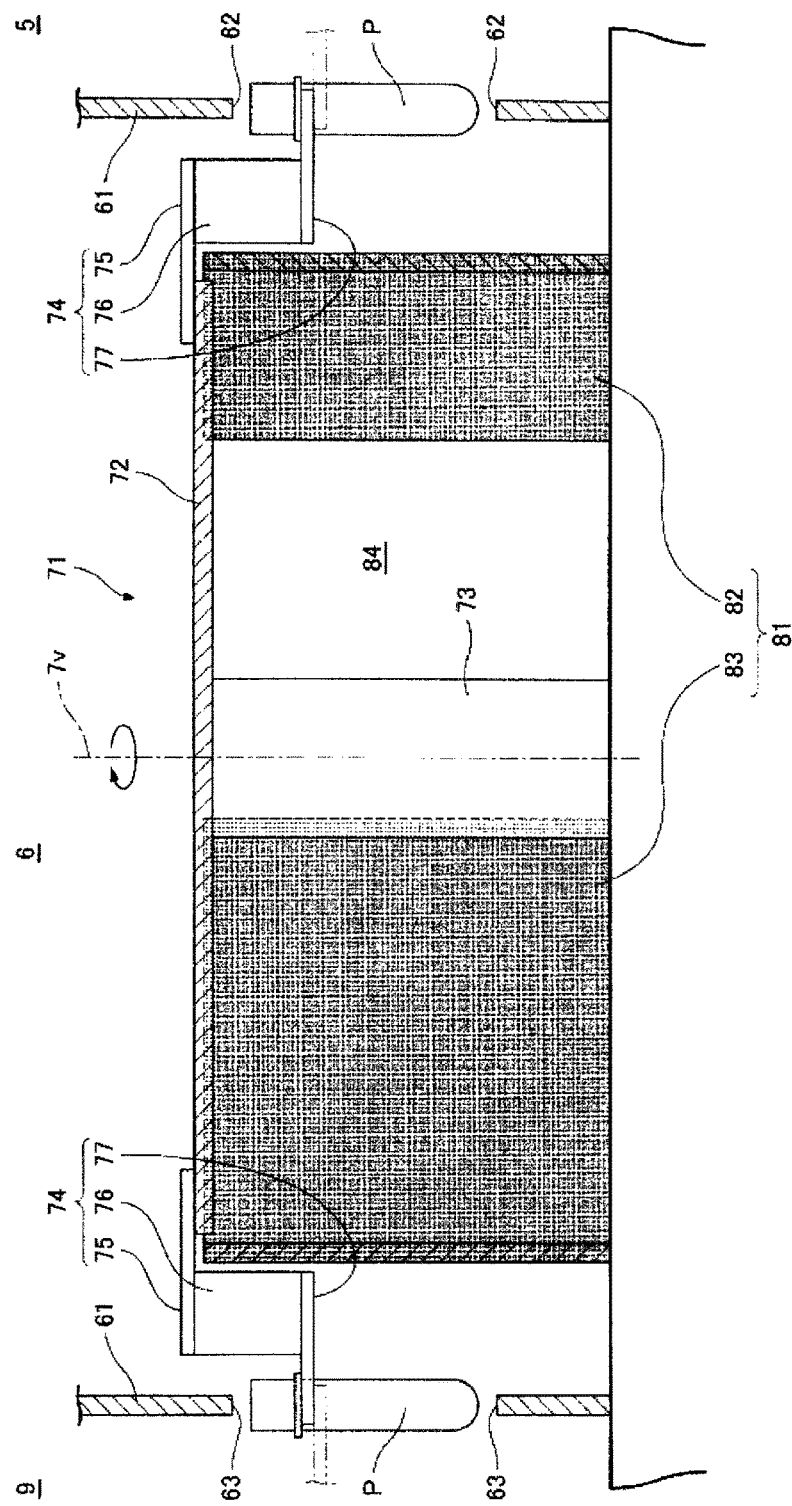
FIG. 5 is a sectional view along the arrows A-A in FIG. 4.

As shown in FIGS. 3 to 5, the blocking chamber 6 may be partitioned with a partition wall 61 from the inner-surface sterilization chamber 5 and the sorting chamber 9 adjacent to the blocking chamber 6. The partition wall 61 may be made of a material that blocks X-rays. The partition wall 61 may have an upstream opening 62 and a downstream opening 63 formed therein. The upstream opening 62 may allow the preform products P to be transferred from the inner-surface sterilization rotation table 53 of the inner-surface sterilization chamber 5 to the sterilized rotation table 71, and the downstream opening 63 may allow the preform products P to be transferred from the sterilized rotation table 71 to the sorting rotation table 91 of the sorting chamber 9. The upstream opening 62 and the downstream opening 63 may have the minimum size that enables transfer of the preform products P, so as to prevent leakage of the X-rays.

The sterilized rotation table 71 may include a circular plate 72 and a drive shaft 73. The circular plate 72 may serve as a table arranged substantially in a horizontal position, and as shown in FIG. 5, the drive shaft 73 may be configured to rotate the circular plate 72 around a vertical axis 7v (the central axis 7v of the circular plate 72). The lower end of the drive shaft 73 may be connected to a drive unit (not shown) provided below the floor of the blocking chamber 6, and the upper end of the drive shaft 73 may be connected to the circular plate 72.

As shown in FIGS. 3 and 5, the grippers 74 provided on the sterilized rotation table 71 may include a connection plate 75, a suspending member 76, and a pair of grip arms 77. The connection plate 75 may extend from the top surface of the periphery of the sterilized rotation table 71 in an outward direction with respect to the central axis 7v. The suspending member 76 may extend downward from the outer end of the connection plate 75. The pair of grip arms 77 may be capable of gripping a preform product P outside the suspending member 76. With this arrangement of the grippers 74, the preform products P may be gripped outside and below the circular plate 72 of the sterilized rotation table 71. Therefore, the upstream opening 62 may also be below the circular plate 72 of the sterilized rotation table 71.

As shown in FIGS. 4 and 5, the blocking walls 81 may include an upstream blocking wall 82 and a downstream blocking wall 83. The upstream blocking wall 82 may face the upstream opening 62 and have an area larger than the upstream opening 62, and the downstream blocking wall 83 may face the downstream opening 63 and have an area larger than the downstream opening 63. Both the upstream blocking wall 82 and the downstream blocking wall 83 may be positioned outside so as to be nearly in contact with the grippers 74. Therefore, as viewed in a plan view shown in FIG. 4, the upstream blocking wall 82 and the downstream blocking wall 83 may be arranged in an arc shape with the central axis 7v at the center thereof and extend so as to cover the upstream opening 62 and the downstream opening 63, respectively. Further, as shown in FIG. 5, the upstream blocking wall 82 and the downstream blocking wall 83 may have a height at least larger than those of the upstream opening 62 and the downstream opening 63, respectively, and may preferably be arranged to be nearly in contact with the grippers 74. The upstream blocking wall 82 and the downstream blocking wall 83 may not contact with the sterilized rotation table 71 as well as the grippers 74.

As shown in FIG. 4, the upstream blocking wall 82 and the downstream blocking wall 83 may not be connected to each other and may be completely separate from each other. That is, there may be formed a space for passing a gas (ozone), or a ventilation space 84, between the upstream blocking wall 82 and the downstream blocking wall 83. The ventilation space 84 may preferably have such a shape and a size that a gas (ozone) can flow smoothly from the upstream opening 62 to the downstream opening 63 (and vice versa), that is, such a shape and a size that the gas (ozone) is less apt to accumulate in the blocking chamber 6. However, the upstream blocking wall 82 and the downstream blocking wall 83 may be arranged to completely interrupt the linear connection between the upstream opening 62 and the downstream opening 63. In other words, the upstream blocking wall 82 and the downstream blocking wall 83 may be positioned to interrupt all the straight lines connecting between the upstream opening 62 and the downstream opening 63. In addition, the upstream blocking wall 82 and the downstream blocking wall 83 may be positioned such that the straight line 2 extending through an end of the upstream opening 62 and an end of the upstream blocking wall 82 may not intersect, in the blocking chamber 6, the straight line 3 extending through an end of the downstream opening 63 and an end of the downstream blocking wall 83. In other words, no straight lines extending through the upstream opening 62 and an end of the upstream blocking wall 82 may intersect, in the blocking chamber 6, any straight lines extending through the downstream opening 63 and an end of the downstream blocking wall 83. In this arrangement, all the X-rays entering through the upstream opening 62 may be reflected three or more times by the blocking walls 81, the partition wall 61, and the like before reaching the downstream opening 63.

The feed chamber 1 which constitutes another purport of the present invention will be described in detail with reference to FIGS. 6 to 7.

Figure 6:
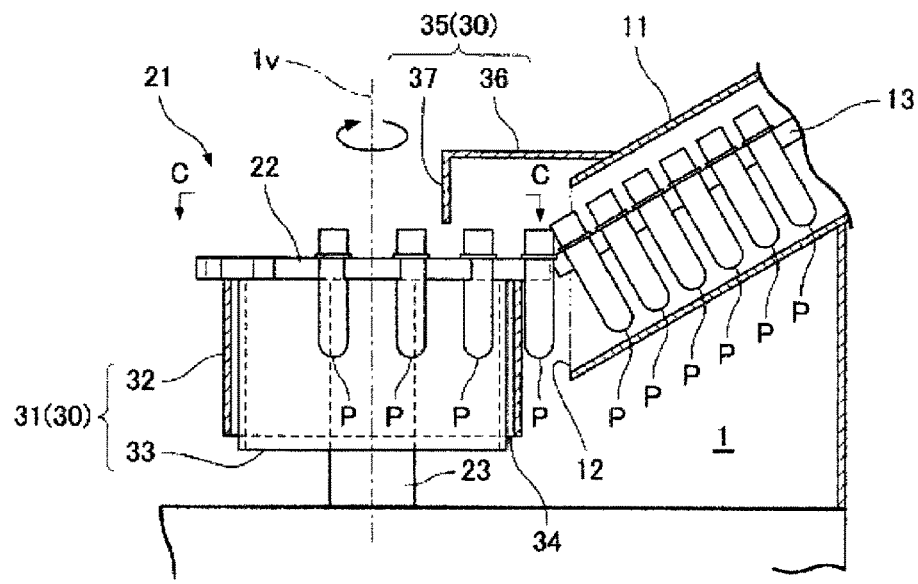
FIG. 6 is a sectional view along the arrows B-B in FIG. 2.

As shown in FIG. 6, the input star wheel 21 may include a star wheel plate 22 and a drive shaft 23. The star wheel plate 22 may be disposed substantially in a horizontal position, and the drive shaft 23 may be configured to rotate the star wheel plate 22 around a vertical axis $1v$ (the central axis $1v$ of the star wheel plate 22). The lower end of the drive shaft 23 may be connected to a drive unit (not shown) provided below the floor of the feed chamber 1, and the upper end of the drive shaft 23 may be connected to the star wheel plate 22.

A guide 13 may be connected to the input star wheel 21 so as to guide the preform products P sliding by the weight thereof through the input tube 11 to the upstream end of the star wheel plate 22. In addition, the input star wheel 21 may include a blocking unit 30 for blocking the X-rays entering from the outer-surface sterilization chamber 4.

The blocking unit 30 may include a blocking short tube 31 (as an example of tubular blocking member) and a blocking roof 35. The blocking short tube 31 may be attached to the lower surface of the star wheel plate 22 and may cover the entire periphery of the drive shaft 23, and the blocking roof 35 may extend from above an opening of the input tube 11 at the downstream side thereof (hereinafter referred to simply as "the feed opening 12") to near the upper surface of the star wheel plate 22. The blocking short tube 31 may prevent the X-rays entering from the outer-surface sterilization chamber 4 from reaching the lower half of the feed opening 12, and the blocking roof 35 may prevent the X-rays entering from the outer-surface sterilization chamber 4 from reaching the upper half of the feed opening 12. Therefore, the blocking short tube 31 and the blocking roof 35 may prevent the X-rays in the feed chamber 1 from leaking harmfully out of the electron beam sterilization apparatus 10 through the input tube 11.

Further, the input tube 11 may be made of a material that blocks X-rays. The inclination angle and the length of the input tube 11 may be designed such that the upper end of the feed opening 12 (that is, the opening of the input tube 11 at the downstream side thereof) is lower than the lower end of the opening of the input tube 11 at the upstream side thereof. Therefore, the X-rays reaching the feed opening may be blocked by the input tube 11. In other words, the input tube 11 may prevent the X-rays in the feed chamber 1 from leaking out of the electron beam sterilization apparatus 10 harmfully.

Figure 7:
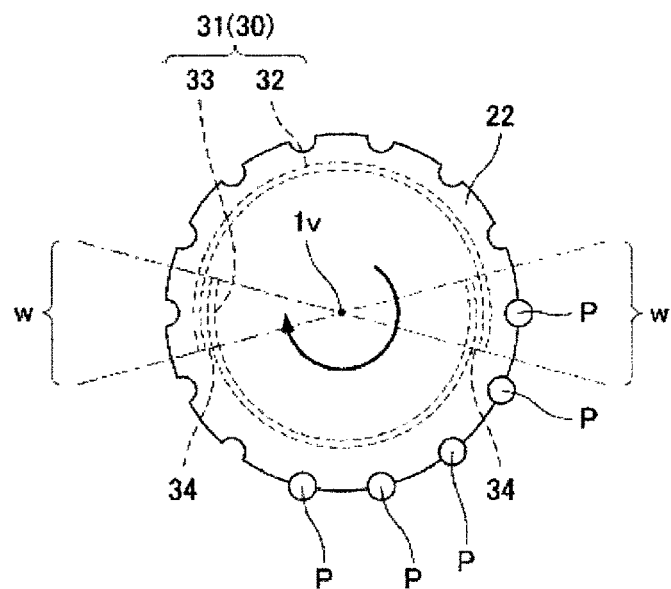
FIG. 7 is viewed along the arrows C-C in FIG. 6.

As shown in FIG. 7, the blocking short tube 31 may include an outer arcuate blocking plate 32 having a larger diameter and an inner arcuate blocking plate 33 having a smaller diameter. Both the outer arcuate blocking plate 32 and the inner arcuate blocking plate 33 may be centered at the central axis $1v$ of the star wheel plate 22 and may have a central angle of 180° or larger in a plan view, and the outer arcuate blocking plate 32 and the inner arcuate blocking plate 33 may overlap each other in the region w as viewed from the central axis $1v$.

The outer arcuate blocking plate 32 and the inner arcuate blocking plate 33 may not be connected to each other and may be completely separated from each other. That is, there may be formed a space for passing a gas (ozone), or a ventilation space 34, between the outer arcuate blocking plate 32 and the inner arcuate blocking plate 33. The ventilation space 34 may preferably have such a shape and a size that a gas (ozone) can flow smoothly from the outer-surface sterilization chamber 4 to the feed opening 12 (and vice versa), that is, such a shape and a size that the gas (ozone) is less apt to accumulate in the feed chamber 1. However, the inner arcuate blocking plate 33 may have such a large diameter as not to be in contact with the outer arcuate blocking plate 32, and the outer arcuate blocking plate 32 may have such a large diameter as to be nearly in contact with the preform products P.

As shown in FIG. 6, the blocking roof 35 may include a horizontal portion 36 and a vertical portion 37. The horizontal portion 36 may project from above the feed opening 12 to above the input star wheel 21 substantially in a horizontal position, and the vertical portion 37 may suspend from the horizontal portion 36 toward the input star wheel 21. The lower end of the vertical portion 37 may be positioned so low as to be nearly in contact with the input star wheel 21 and the preform products P conveyed thereby.

The operation of the electron beam sterilization apparatus 10 will be hereinafter described.

As shown in FIG. 2, the preform products P fed into the feed chamber 1 may sequentially be conveyed to the outer-surface sterilization chamber 4, the inner-surface sterilization chamber 5, the blocking chamber 6, and the sorting chamber 9, and may then be fed to the external apparatus F from the sorting chamber 9. While being conveyed, the preform products P may have the outer surfaces thereof sterilized with the electron beams in the outer-surface sterilization chamber 4 and have the inner surfaces thereof sterilized with the electron beams in the inner-surface sterilization chamber 5. In the outer-surface sterilization chamber 4 and the inner-surface sterilization chamber 5, the electron beams may be applied to the preform products P for electron beam sterilization, and as a result, X-rays may be produced. Further, in the outer-surface sterilization chamber 4 and the inner-surface sterilization chamber 5, the electron beams may cause a chemical reaction of the air that undesirably produces ozone.

The X-rays produced in the outer-surface sterilization chamber 4 and the inner-surface sterilization chamber 5 may enter the blocking chamber 6 and the feed chamber 1 adjacent thereto. The X-rays, which may possibly leak out of the electron beam sterilization apparatus 10, may be blocked in the blocking chamber 6 and the feed chamber 1 and prevented from leaking out harmfully. Meanwhile, the ozone gas produced in the outer-surface sterilization chamber 4 and the inner-surface sterilization chamber 5 may also enter the blocking chamber 6 and the feed chamber 1 having complex structures such as the blocking walls 81 and the blocking unit 30. However, since the ozone gas in the blocking chamber 6 and the feed chamber 1 may flow smoothly because of the ventilation spaces 84, 34, the ozone gas may be less apt to accumulate in the block chamber 6 and the feed chamber 1 and may be discharged from the electron beam sterilization apparatus 10 by the ventilator.

The blocking chamber 6 and the feed chamber 1 will be hereinafter individually described.

As shown in FIG. 4, the X-rays entering the blocking chamber 6 through the upstream opening 62 may be blocked by the blocking walls 81 and reflected by the blocking walls 81, the partition wall 61, and the like (the floor, walls, ceiling, etc. of the blocking chamber 6). As a result, the X-rays are attenuated. Because of the arrangement of the blocking walls 81 described above, all the X-rays entering through the upstream opening 62 may be reflected three or more times by the blocking walls 81, the partition wall 61, and the like before reaching the downstream opening 63, and thus may be attenuated to be harmless.

As shown in FIGS. 2 and 6, the X-rays entering the feed chamber 1 from the outer-surface sterilization chamber 4 may be blocked by the blocking unit 30 and reflected by the blocking unit 30 and the like (the floor, walls, ceiling, etc. of the feed chamber 1). As a result, the X-rays are attenuated. Because of the arrangement of the blocking unit 30 described above, all the X-rays entering from the outer-surface sterilization chamber 4 may be reflected three or more times by the blocking unit 30 and the like before reaching the feed opening 12, and thus may be attenuated to be harmless.

Thus, in the electron beam sterilization apparatus 10, the blocking walls 81 having a large weight may not be attached to the sterilized rotation table 71, and therefore, the sterilized rotation table 71 and other rotation tables 51, 53, 91, and 93 may be rotated at a high speed, thereby enabling high speed operation.

In addition, the X-rays can be blocked sufficiently in the blocking chamber 6 and the feed chamber 1 alone, and therefore, the electron beam sterilization apparatus 10 may not need to include other chambers or structures for blocking the X-rays and thus can be downsized. Further, the electron beam sterilization apparatus 10, having fewer chambers, may tend to have less ozone gas accumulated therein, and thus can be prevented from corrosion.

In addition, because of the ventilation spaces 34, 84, the electron beam sterilization apparatus 10 may tend to have less ozone gas accumulated therein, and thus can be prevented from corrosion.

In the above description, the preform products P were taken as an example of container. The present invention can also be applied for plastic bottles B or other containers.

In the above embodiment, the grippers 74 were taken as an example of retainer, but the present invention can use any other retainers that can retain the containers.

Further, in the above embodiment, the blocking walls 81 may be positioned outside so as to be nearly in contact with the grippers 74. Therefore, the blocking walls 81 may be arranged within a region outward from the periphery of the sterilized rotation table 71. For example, the blocking walls 81 may be positioned under the portion of the connection plate 75 attached to the sterilized rotation table 71 (that is, in the periphery of the sterilized rotation table 71).

Figure 8:
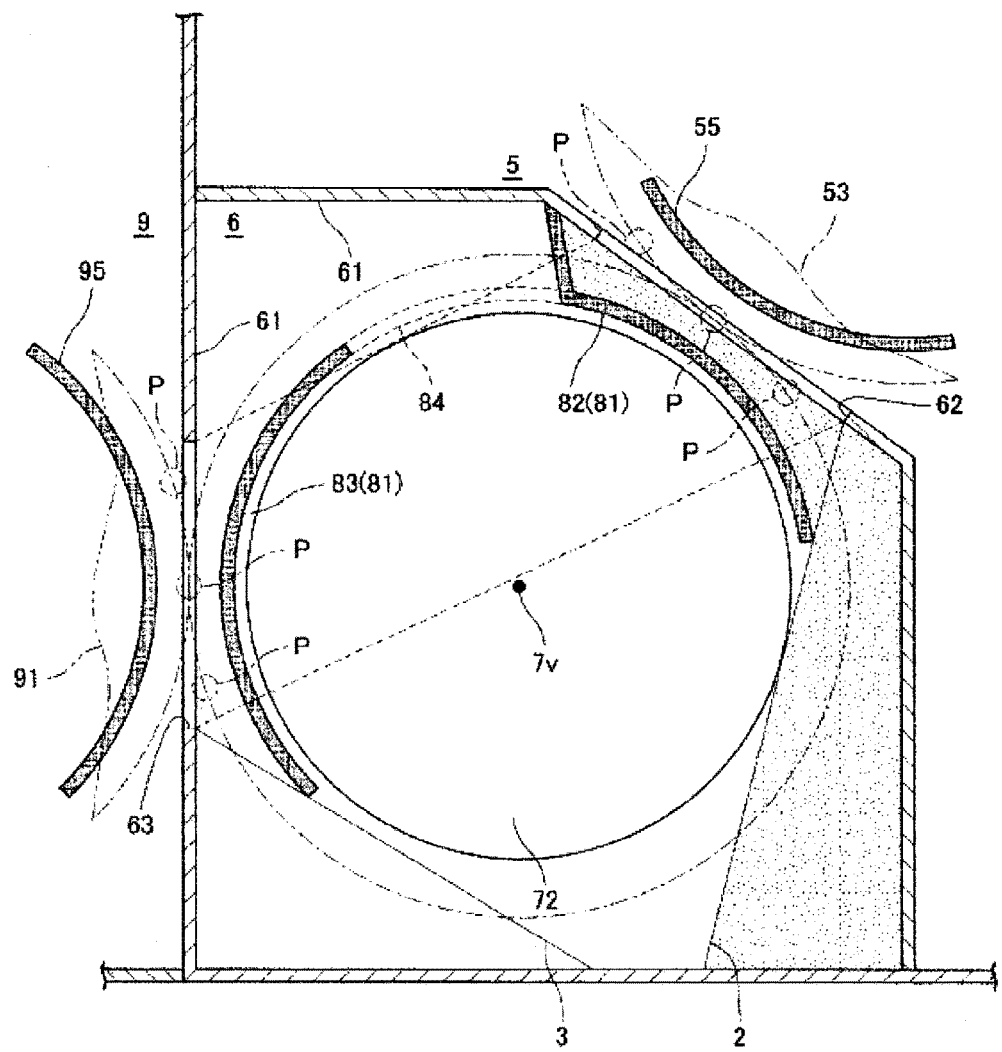
FIG. 8 is a plan view of a variation of the blocking chamber.

In addition, the sorting chamber 9 of the above embodiment can include a blocking wall which was not described for the above embodiment. As shown in FIG. 8, the sorting chamber 9 may include a blocking wall 95 arranged such that the blocking wall 95 and the downstream blocking wall 83 are in line symmetry with respect to the partition wall 61 between the blocking chamber 6 and the sorting chamber 9. This arrangement may further facilitate sufficient blocking of the X-rays. It may also be possible that the downstream blocking wall 83 is omitted when the sorting chamber 9 includes the blocking wall 95.

In addition, the inner-surface sterilization chamber 5 of the above embodiment can include a blocking wall which was not described for the above embodiment. As shown in FIG. 8, the inner-surface sterilization chamber 5 may include a blocking wall 55 arranged such that the blocking wall 55 and the upstream blocking wall 82 are in line symmetry with respect to the partition wall 61 between the inner-surface sterilization chamber 5 and the blocking chamber 6. This arrangement may further facilitate sufficient blocking of the X-rays. It may also be possible that the upstream blocking wall 82 is omitted when the inner-surface sterilization chamber 5 includes the blocking wall 55.

Figure 9:
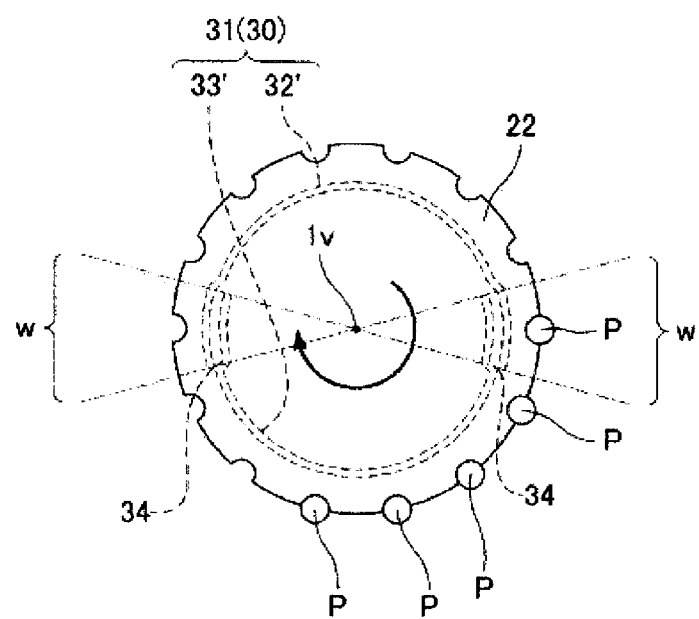
FIG. 9 is a plan view of a variation of an input star wheel in the electron beam sterilization apparatus.

In the above embodiment, the blocking short tube 31 may include an outer arcuate blocking plate 32 having a larger diameter and an inner arcuate blocking plate 33 having a smaller diameter. It may also be possible that, as shown in FIG. 9, the blocking short tube 31 includes arcuate blocking plates 32', 33' having the same diameter, as long as it has a ventilation space 34 and the overlapping region w. It may also be possible that the blocking short tube 31 includes three or more arcuate blocking plates, instead of two arcuate blocking plates. Alternatively, the blocking short tube 31 may have an integral structure, as long as it has a cutout serving as a ventilation space 34.

The shape of the blocking walls 81 described for the above embodiment is not limitative. The blocking walls 81 need only to face the upstream opening 62 or the downstream opening 63 and have a larger area than the upstream opening 62 or the downstream opening 63 facing thereto.

The suspending member 76 of the gripper 74, which was not described in detail for the above embodiment, may be made of a material that blocks X-rays. This arrangement may further facilitate sufficient blocking of the X-rays.

What is claimed is:

1. An electron beam sterilization apparatus for sterilizing a container by applying an electron beam while conveying the container, the apparatus comprising:
   a sterilization chamber including an electron beam application device for applying an electron beam to a container; and
   a blocking chamber for receiving the container from the sterilization chamber and blocking radioactive rays produced by application of the electron beam,
   wherein the blocking chamber includes an upstream opening and a downstream opening formed therein, the container being received from the sterilization chamber through the upstream opening and transferred to outside of the blocking chamber through the downstream opening,
   the blocking chamber includes:
      a retainer for retaining the container;
      a rotation table for conveying the container retained by the retainer in a circular path; and
      at least one blocking wall not in contact with the rotation table and configured to block the radioactive rays from the sterilization chamber, and the at least one blocking wall faces the upstream opening or the downstream opening and has a larger area than the upstream opening or the downstream opening facing thereto,
   the at least one blocking wall is arranged within a region inside of a circular path in which the container is conveyed by the rotation table, and
   wherein the at least one blocking wall extends higher than upper ends of the upstream opening and the downstream opening.

2. The electron beam sterilization apparatus of claim 1, wherein the at least one blocking wall comprises an upstream blocking wall and a downstream blocking wall, the upstream blocking wall facing the upstream opening and having an area larger than the upstream opening, the downstream blocking wall facing the downstream opening and having an area larger than the downstream opening.

3. The electron beam sterilization apparatus of claim 2, wherein a ventilation space is formed between the upstream blocking wall and the downstream blocking wall.

4. The electron beam sterilization apparatus of claim 2, wherein the upstream blocking wall and the downstream blocking wall are positioned to block all straight lines connecting between the upstream opening and the downstream opening.

5. The electron beam sterilization apparatus of claim 2, wherein no straight lines extending through the upstream opening and an end of the upstream blocking wall intersect, in the blocking chamber, any straight lines extending through the downstream opening and an end of the downstream blocking wall.

* * * * *